(12) United States Patent
Deppmeier et al.

(10) Patent No.: US 7,160,247 B2
(45) Date of Patent: Jan. 9, 2007

(54) ENDOSCOPE WITH LARGE DIAMETER DISTAL END

(75) Inventors: Thomas R. Deppmeier, Buellton, CA (US); Craig J. Speier, Santa Barbara, CA (US); Josiah E. Verkaik, Morro Bay, CA (US); Robert R. Walls, Santa Barbara, CA (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 10/918,187

(22) Filed: Aug. 13, 2004

(65) Prior Publication Data

US 2005/0256377 A1 Nov. 17, 2005

Related U.S. Application Data

(60) Provisional application No. 60/570,276, filed on May 12, 2004.

(51) Int. Cl.
- A61B 1/00 (2006.01)
- A61B 1/04 (2006.01)
- A61B 1/06 (2006.01)

(52) U.S. Cl. .............. 600/129; 600/138; 600/171; 600/182

(58) Field of Classification Search ........... 600/114, 600/129, 136, 138, 153–159, 171, 182, 435
See application file for complete search history.

(56) References Cited

U.S. PATENT DOCUMENTS

| | | | |
|---|---|---|---|
| 4,138,192 A | 2/1979 | Yamasita | |
| 4,415,240 A * | 11/1983 | Nishioka et al. | ............... 385/33 |
| 4,515,444 A | 5/1985 | Prescott et al. | |
| 4,655,557 A | 4/1987 | Takahashi | |
| 4,684,224 A | 8/1987 | Yamashita et al. | |
| 4,783,156 A | 11/1988 | Yokota | |
| 4,815,833 A | 3/1989 | Zobel et al. | |
| 4,850,342 A | 7/1989 | Hashiguchi et al. | |
| 4,964,710 A | 10/1990 | Leiner | |
| 4,969,708 A | 11/1990 | Leiner | |
| 5,156,142 A | 10/1992 | Anapliotis et al. | |
| 5,198,931 A | 3/1993 | Igarashi | |
| 5,199,417 A | 4/1993 | Muller et al. | |
| 5,278,679 A | 1/1994 | Davis et al. | |
| 5,337,734 A | 8/1994 | Saab | |
| 5,377,669 A | 1/1995 | Schulz | |
| 5,418,649 A | 5/1995 | Igarashi | |
| 5,456,673 A | 10/1995 | Ziegler et al. | |
| 5,477,389 A | 12/1995 | Ito et al. | |
| 5,509,892 A * | 4/1996 | Bonnet | ............ 600/156 |
| 5,573,493 A * | 11/1996 | Sauer et al. | ............ 600/121 |
| 5,734,511 A * | 3/1998 | Braat | ............ 359/716 |
| 5,793,539 A | 8/1998 | Konno et al. | |
| 5,796,528 A | 8/1998 | Mihara | |
| 5,807,240 A * | 9/1998 | Muller et al. | ............ 600/135 |
| 5,828,498 A | 10/1998 | Sekiya et al. | |
| 5,830,126 A * | 11/1998 | Odanaka et al. | ............ 600/156 |
| 5,936,778 A | 8/1999 | Miyano et al. | |

(Continued)

Primary Examiner—John Leubecker
Assistant Examiner—Philip R Smith
(74) Attorney, Agent, or Firm—Howrey LLP

(57) ABSTRACT

An endoscope is described in which the diameter of the image relay assembly is less than that of the objective lens assembly. An endoscope sheath is also described for sheathing the endoscope and housing or directing optical fibers for use in illuminating the endoscope view of view. An endoscope-sheath system is further described comprising the combination of the endoscope and the endoscope sheath.

55 Claims, 8 Drawing Sheets

U.S. PATENT DOCUMENTS

| | | |
|---|---|---|
| 5,999,337 A | 12/1999 | Ozaki |
| 6,057,971 A | 5/2000 | Mihara |
| 6,126,592 A * | 10/2000 | Proch et al. ............... 600/114 |
| 6,222,685 B1 | 4/2001 | Yamada |
| 6,478,731 B1 | 11/2002 | Speier et al. |
| 6,498,884 B1 | 12/2002 | Colvin et al. |
| 6,589,165 B1 | 7/2003 | Bodor et al. |
| 6,618,207 B1 | 9/2003 | Lei |
| 6,635,010 B1 | 10/2003 | Lederer |
| 6,645,140 B1 * | 11/2003 | Brommersma ............... 600/128 |
| 6,761,684 B1 * | 7/2004 | Speier ....................... 600/121 |
| 2001/0023314 A1 | 9/2001 | Bodor et al. |

* cited by examiner

ENDOSCOPE WITH LARGE DIAMETER DISTAL END

This application claims the benefit of U.S. Provisional Application Ser. No. 60/570,276, entitled "Endoscope-Sheath System," filed May 12, 2004, which is hereby fully incorporated by reference herein as though set forth in full.

FIELD OF THE INVENTION

This invention relates to the field of endoscopes, and, more specifically, high definition endoscopes that allow higher resolution viewing of internal body structures compared to conventional endoscopes.

RELATED ART

A high definition endoscope is needed to allow higher resolution viewing of internal body structures in relation to conventional endoscopes, and to match that available in current broadcast cameras. However, the increased size, surgical invasiveness, and obstruction in fluid flow that results from increasing the diameter of the objective lens or objective lens assembly in the endoscope weighs against such an approach.

SUMMARY OF THE INVENTION

In accordance with a first aspect of the invention, an endoscope comprises an intermediate portion having a distal end. One or more optical elements form an objective lens assembly disposed at or within the distal end. One or more optical elements form an image relay assembly disposed at or within the intermediate portion and situated along an optical path extending from the objective lens assembly. The diameter of the image relay assembly is less than that of the objective lens assembly.

In accordance with a second aspect of the invention, an endoscope sheath comprises a body portion and a tip portion. The tip portion has a distal end, an intermediate sub-portion, and a proximal end. The tip portion is affixed to or integral with the body portion at the proximal end. The tip portion comprises inner and outer cylinders eccentrically arranged to contact one another at one or more planes of tangency, and thus form one or more annular gaps in between the inner and outer cylinders.

A plurality of optical fibers extends lengthwise through the one or more annular gaps from the distal end of the tip portion to an illumination port in the intermediate sub-portion. A fluid ingress port in the intermediate sub-portion is located distally in relation to the illumination port.

In accordance with a third aspect of the invention, an endoscope-sheath system comprises an endoscope, an endoscope sheath sheathing at least a portion of the endoscope, and a body.

The endoscope comprises a distal end and a proximal end, wherein the distal end is metal and brazed to a distal window.

The endoscope sheath comprises a distal end, an intermediate portion, and a proximal end. The sheath further comprises inner and outer cylinders eccentrically arranged to contact one another at one or more planes of tangency, and form one or more annular gaps in between the inner and outer cylinders. A plurality of optical fibers extends lengthwise through the one or more annular gaps from the distal end through at least a part of the intermediate portion.

The body is affixed to or integral with the proximal ends of the endoscope and endoscope sheath.

In accordance with a fourth aspect of the invention, an endoscope-sheath system comprises an endoscope, an endoscope sheath sheathing at least a portion of the endoscope, and a body.

The endoscope comprises an intermediate portion having a distal end and a proximal end. One or more optical elements form an objective lens assembly disposed at or within the distal end. One or more optical elements form an image relay assembly disposed at or within the intermediate portion and situated along an optical path extending from the objective lens assembly. The diameter of the image relay assembly is less than that of the objective lens assembly.

The endoscope sheath comprises a distal end, an intermediate portion, and a proximal end. The sheath further comprises inner and outer cylinders eccentrically arranged to contact one another at one or more planes of tangency, and form one or more annular gaps in between the inner and outer cylinders. A plurality of optical fibers extends lengthwise through the one or more annular gaps from the distal end through at least a part of the intermediate portion.

The body is affixed to or integral with the proximal ends of the endoscope and endoscope sheath.

Related systems, methods, features and advantages of the invention or combinations of the foregoing will be or will become apparent to one with skill in the art upon examination of the following figures and detailed description. It is intended that all such additional systems, methods, features, advantages and combinations be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION

As utilized herein, terms such as "about," "approximately," "substantially" and "near" are intended to allow some leeway in mathematical exactness to account for tolerances that are acceptable in the trade. Accordingly, any deviations upward or downward from the value modified by the terms "about," "approximately," "substantially" or "near" in the range of 1% to 20% or less should be considered to be explicitly within the scope of the stated value.

Figure 1:
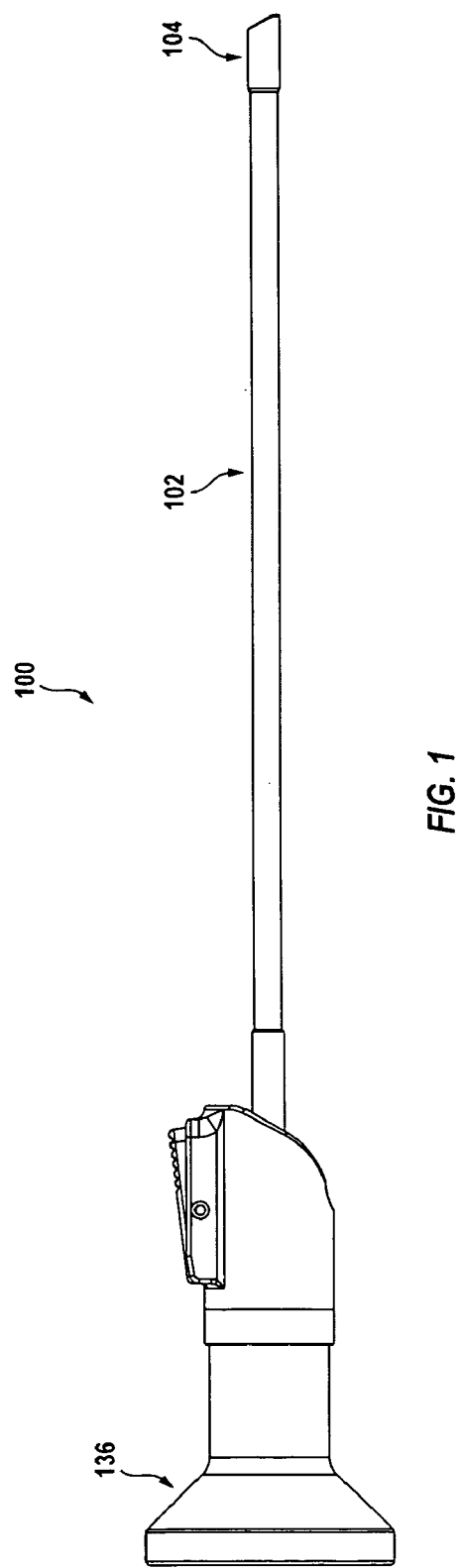
FIG. 1 is a side view of an embodiment of an endoscope in accordance with the invention.
Figure 2:
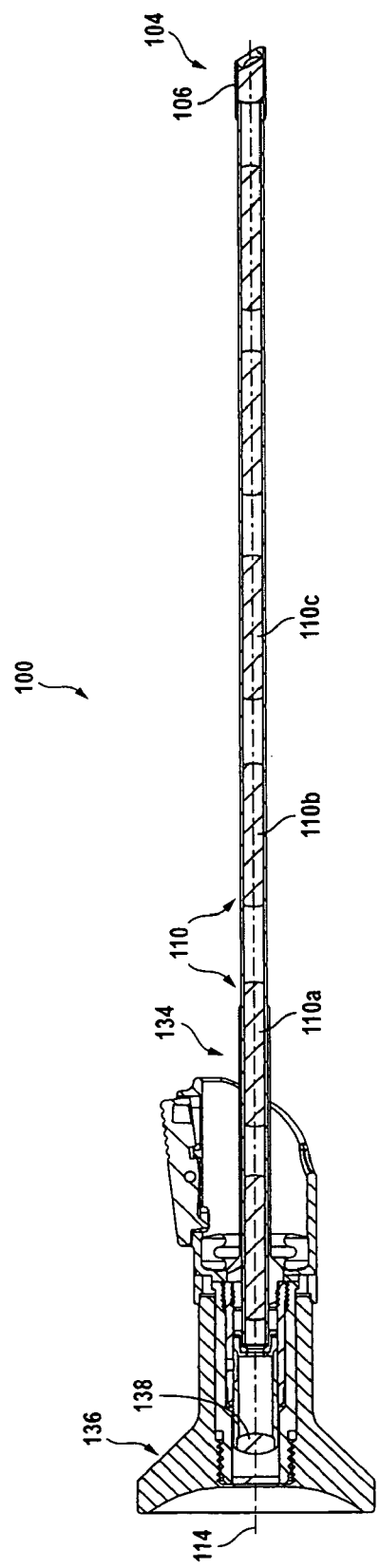
FIG. 2 is the cross-sectional side view of the endoscope of FIG. 1.
Figure 3:
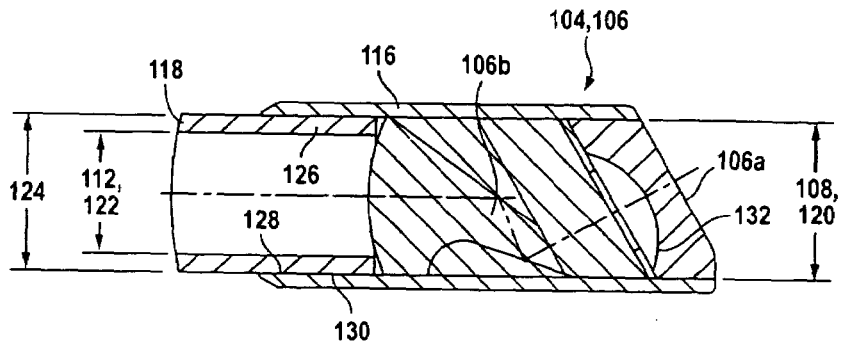
FIG. 3 is a cross-sectional side view of the detail B of FIG. 2.
Figure 5:
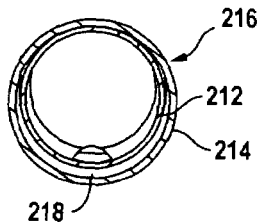
FIG. 5 is the cross-sectional end view C—C of the endoscope sheath of FIG. 4.
Figure 7:
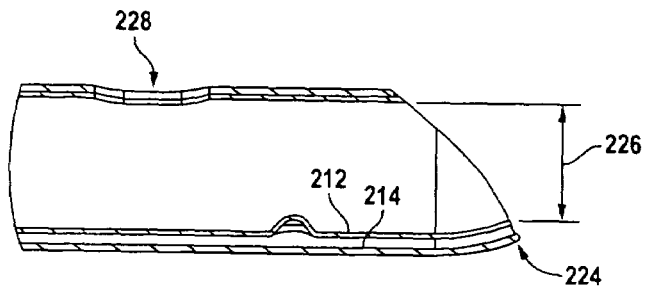
FIG. 7 is a cross-sectional side view of the detail E of FIG. 6.
Figure 8:
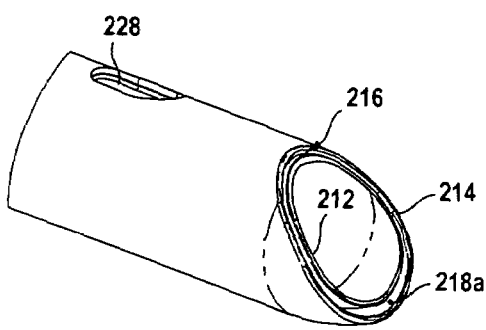
FIG. 8 is a plan view of FIG.7.
Figure 4:
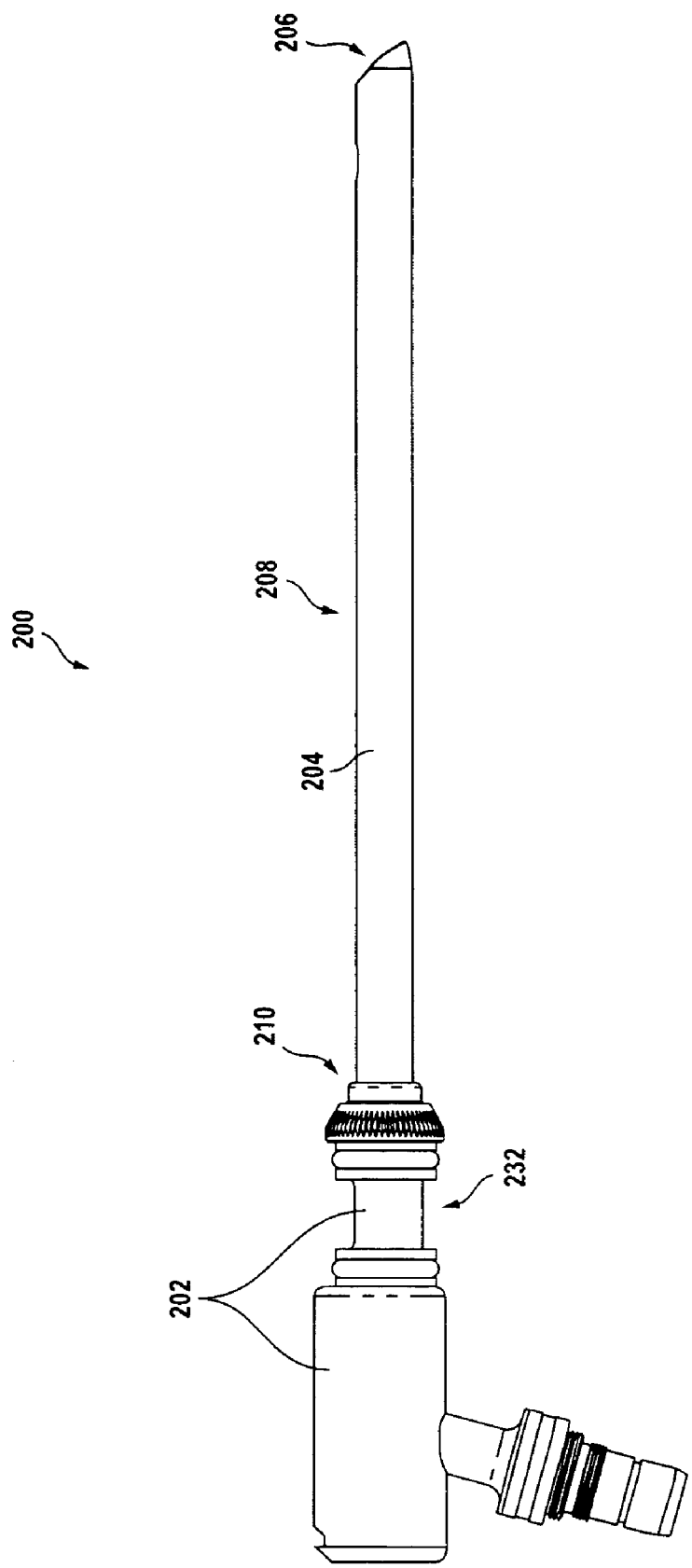
FIG. 4 is a side view of an embodiment of an endoscope sheath in accordance with the invention.
Figure 6:
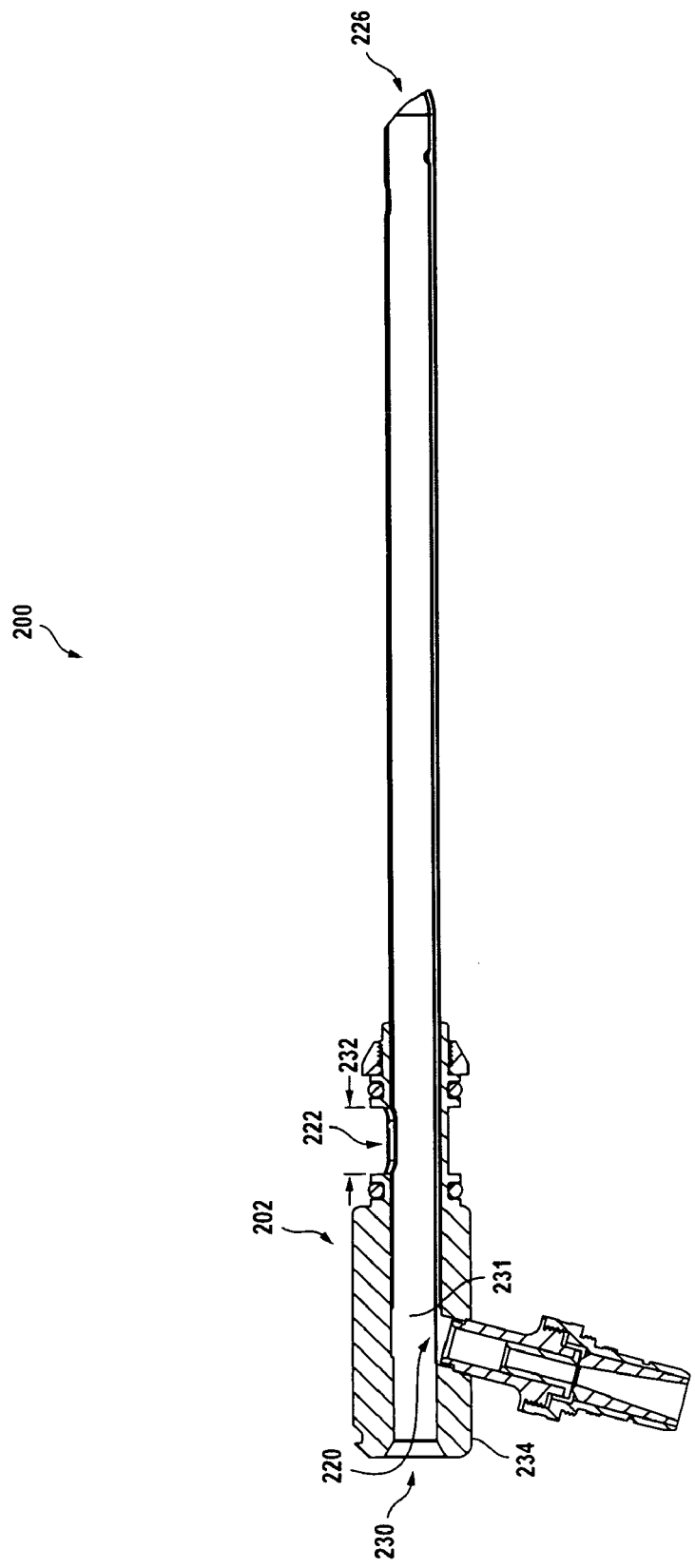
FIG. 6 is the cross-sectional side view of the endoscope sheath of FIG. 4.
Figure 9:
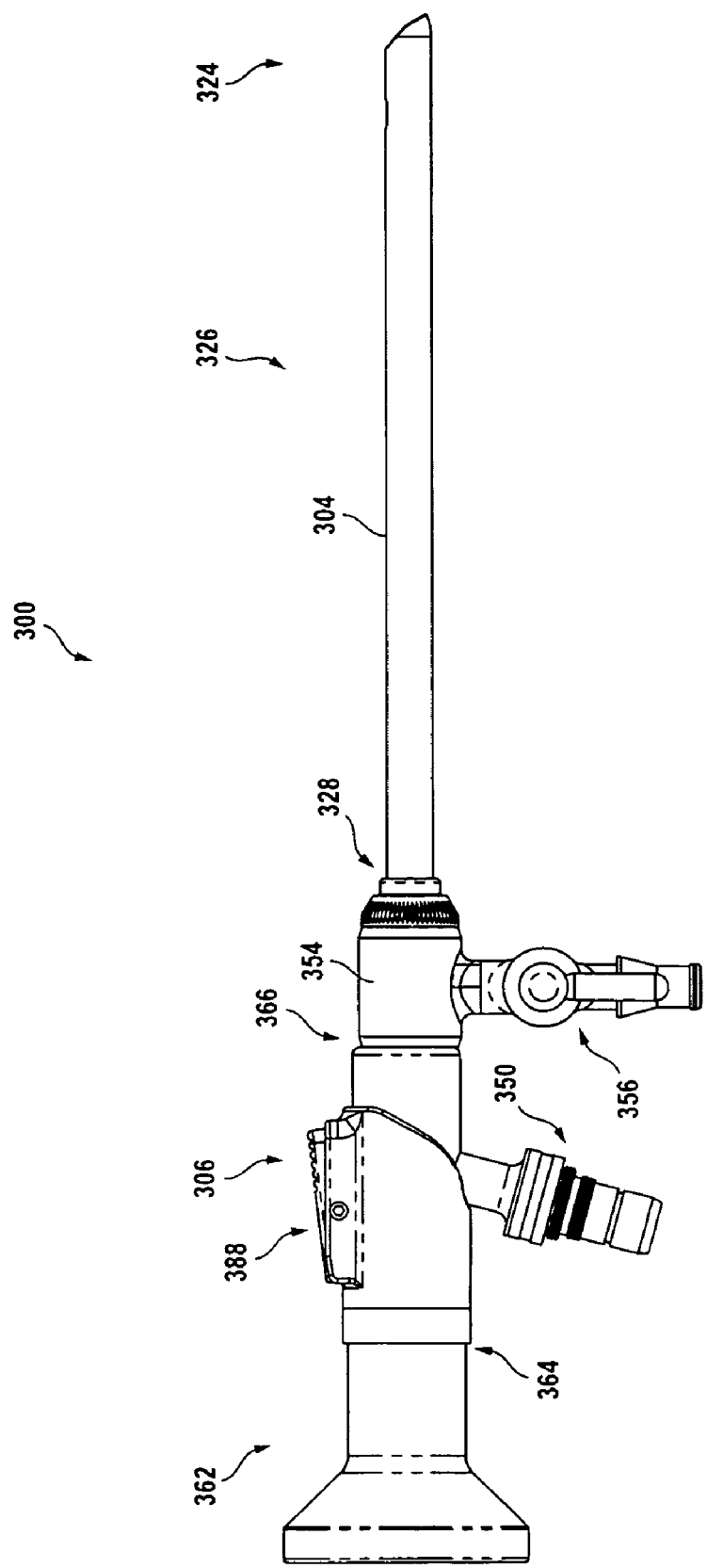
FIG. 9 is a side view of an embodiment of an endoscope-sheath system.
Figure 10:
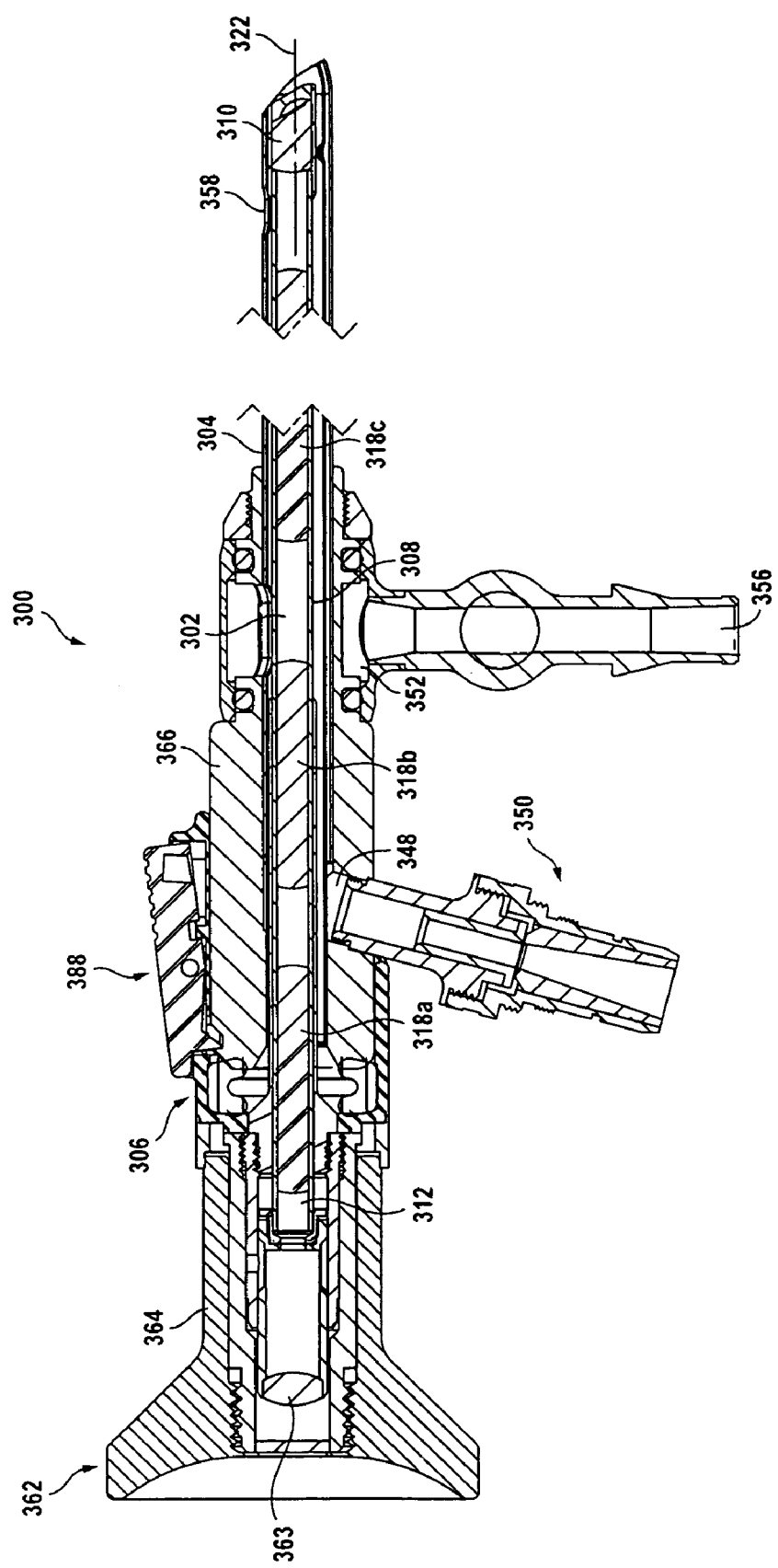
FIG. 10 is the cross-sectional side view of the system of FIG. 9.
Figure 11:
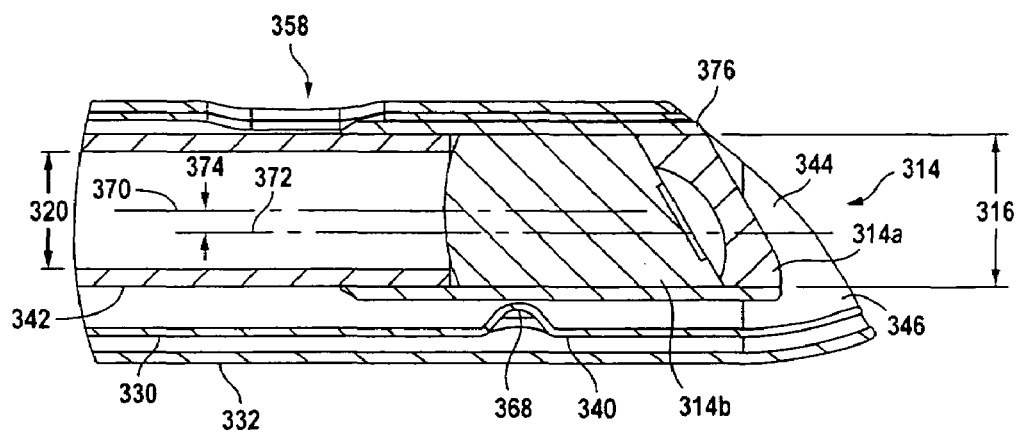
FIG. 11 is a cross-sectional side view of the detail J of FIG. 10.
Figure 12:
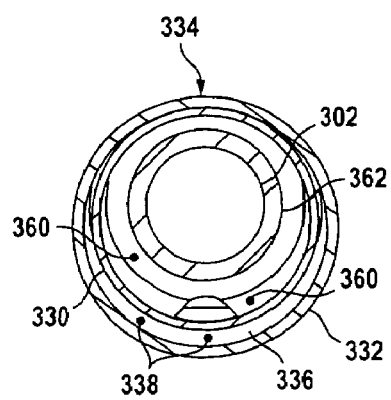
FIG. 12 is the cross-sectional end view K—K of the system of FIG. 9.

FIGS. 1–3 illustrate an embodiment of an endoscope 100 comprising an intermediate portion 102 having a distal end 104. One or more optical elements 106a, 106b form an objective lens assembly 106 having a first diameter 108, the objective lens assembly 106 disposed at or within the distal end 104.

One or more optical elements 110a, 110b, 110c form an image relay assembly 110 having a second diameter 112 less than the first diameter 108. The image relay assembly 110 is disposed at or within the intermediate portion 102 and situated along an optical path 114 extending from the objective lens assembly 106 through at least a portion of the endoscope 100.

In one implementation, the distal end 104 at least partially houses the objective lens assembly 106, and the intermediate portion 102 at least partially houses the image relay assembly 110.

In one implementation example, the distal end 104 is a tube or tube segment 116 at least partially housing the objective lens assembly 106, and the intermediate portion 102 is a tube or tube segment 118 at least partially housing the image relay assembly 110.

In this implementation example, the distal end tube or tube segment 116 has an inner diameter 120 defining the first diameter 108 of the objective lens assembly 104, and the intermediate portion tube or tube segment 118 has an inner diameter 122 defining the second diameter 112 of the image relay assembly 110.

In one configuration, the intermediate portion tube or tube segment 118 has an outer diameter 124 approximately equal to the inner diameter 120 of the distal end tube or tube segment 116, and the distal tube or tube segment 116 closely receives in axial alignment an interface portion 126 of the intermediate tube or tube segment 118.

In this configuration, the distal end tube or tube segment 116 has an inner surface 128 adhered to an outer surface 130 of the interface portion 128 of the intermediate portion tube or tube segment 118.

In one example, the distal end tube or tube segment 116 is a metal tube or tube segment, and the inner surface 128 thereof is welded or fillet welded to the outer surface 130 of the interface portion 126 of the intermediate portion tube or tube segment 118, also a metal tube or tube segment in this example.

In one embodiment, the distal end 104 has a distal window 106a through which light reflected from an object in the field of the view of the endoscope enters the endoscope. In one implementation, the distal window 106a is adhered to the distal end tube or tube housing 116. In one implementation example, the distal end 104 comprises a metal tube or tube segment 116 and the distal window 106a is brazed or high temperature brazed to the distal end tube or tube segment 116.

In one configuration, the distal window 106a is composed of glass or sapphire. In a second configuration, the distal window 106a is one of the optical elements in the objective lens assembly 106. In a third configuration, the one or more optical elements of the objective lens assembly 106 form an integral unit.

In one example, the one or more optical elements of the objective lens assembly 106 comprise the distal window 106a configured with a negative interior surface 132, and a prism 106b adhered to at least part of the negative interior surface 132 of the distal window 106a.

In one embodiment, the endoscope 100 has a proximal end 134 attached to or integral with a proximal eyepiece 136 for viewing images. In one implementation, the eyepiece 136 includes a proximal ocular lens 138 situated along the optical path 114 extending from the objective lens assembly 106.

In one embodiment, the image relay assembly 110 comprises one or more rod lenses 110a, 110b, 110c. In a second embodiment, the image relay assembly 110 comprises a plurality of optical fibers.

FIGS. 4–8 illustrate an embodiment of an endoscope sheath 200 comprising a body portion 202 and a tip portion 204. In this embodiment, the tip portion 204 has a distal end 206, an intermediate sub-portion 208, and a proximal end 210. Also in this embodiment, the proximal end 210 is affixed to or integral with the body portion 202.

The tip portion 204 comprises inner and outer cylinders, respectively identified with numerals 212, 214, eccentrically arranged to contact one another at one or more planes or points of tangency 216, thus forming one or more annular gaps 218 in between the inner and outer cylinders 212, 214.

In this embodiment, a plurality of optical fibers (not shown) extend lengthwise through the one or more annular gaps 218 from the distal end 206 of the tip portion 204 to one or more illumination ports 220 at the proximal end 210 or in the intermediate sub-portion 208. In addition, one or more fluid ingress ports 222 at the proximal end 210 or in the intermediate sub-portion 208 are located distally in relation to the one or more illumination ports 220.

In one implementation, the distal end 206 has an end form 224 that angles a distal opening 226 towards a desired viewing field. In addition, in this implementation, the end form 224 also angles the one or more annular gaps 218a between the inner and outer cylinders at the distal opening 226 towards the desired viewing field.

In one implementation example, one or more of the plurality of optical fibers have polished ends (not shown) flush with and terminating at the distal opening 226. Also, the one or more annular gaps 218a at the distal opening 226 may be epoxy filled.

In one embodiment, the endoscope sheath 200 further comprises one or more fluid egress ports 228 in the intermediate sub-portion 208 of the tip portion 204. In one implementation, the one or more fluid egress ports 228 are located at one or more points or planes of tangency 216 between the inner and outer cylinders 212, 214. In one example, the one or more fluid egress ports 228 are located near the distal end 206 of the tip portion 204.

In one embodiment, the inner and outer cylinders 212, 214 are each circular, and contact one another at a single point or plane of tangency. In another embodiment, one or both of the inner and outer cylinders 212, 214 are non-circular, i.e., elliptical, and may contact each other at more than one point or plane of tangency.

In one implementation, the body portion 202 is recessed to receive the proximal end 210 of the tip portion 204. In one implementation example, the body portion 202 has a proximal opening 230 that extends to the proximal end 210 of the tip portion 204.

In one implementation, the one or more fluid ingress ports 222 is an opening in both cylinders 212, 214. In one embodiment, the endoscope sheath 200 also comprises an interface 232 to one or more fluid communication components (not shown in FIGS. 4–8). In one example, the interface 232 is a rotatable and detachable stopcock collar.

In one configuration, the one or more illumination ports 220 extend from a recess 231 in the body portion 202 to an exterior surface 234 of the body portion 202. In one example, the one or more illumination ports 220 comprise openings in the outer cylinder 214 allowing optical coupling between light from one or more illumination components and proximal ends of one or more of the optical fibers in the one or more annular gaps 218 between the inner and outer cylinders.

FIGS. 9–12 illustrates an embodiment of an endoscope-sheath system 300, an endoscope 302, an endoscope sheath 304, and a body 306.

In this embodiment, the endoscope 304 comprises an intermediate portion 308 having a distal end 310 and a proximal end 312. In one implementation, the endoscope further comprises: (1) one or more optical elements 314a, 314b forming an objective lens assembly 314 having a first diameter 316, the objective lens assembly 314 disposed at or within the distal end 310; and (2) one or more optical elements 318a, 318b, 318c forming an image relay assembly having a second diameter 320 less than the first diameter 316, the image relay assembly disposed at or within the intermediate portion 308 and situated along an optical path 322 extending from the objective lens assembly 314. In a second implementation, the distal end 310 of the endoscope is metal and brazed to a distal window 314a through which light reflected from an object in the field of the view of the endoscope enters the endoscope.

The endoscope sheath 304 sheathes at least a portion of the endoscope 304, and comprises: (1) a distal end 324, an intermediate portion 326, and a proximal end 328, with inner and outer cylinders, identified with numerals 330, 332 respectively, eccentrically arranged to contact one another at one or more points or planes of tangency 334, thus forming one or more annular gaps 336 in between the inner and outer cylinders 330, 332; and (2) a plurality of optical fibers 338 extending lengthwise through the one or more annular gaps 336 from the distal end 324 through at least a part of the intermediate portion 326.

The body 306 is affixed to or integral with the proximal ends of the endoscope and endoscope sheath, identified respectively with numerals 312, 328.

In one implementation, the endoscope distal end 310 is a tube or tube segment 340 at least partially housing the objective lens assembly 314, and the endoscope intermediate portion 302 is a tube or tube segment 342 at least partially housing the image relay assembly.

In one implementation example, the endoscope distal end 310 has a distal window 314a through which light reflected from an object in the field of the view of the endoscope enters the endoscope. In one configuration, the distal window 314a is adhered to the endoscope distal end tube or tube housing 340. In one example, the endoscope distal end 310 comprises a metal tube or tube segment to which is brazed the distal window 314a. The distal window 314a may be composed of glass or sapphire. In one example, the distal window 314a is situated within or optically coupled to a sheath distal opening 344. In a second example, the sheath distal end 324 has an end form 346 that angles the distal opening 344 towards a desired viewing field. In a third example, the end form 346 also angles the one or more annular gaps 336 between the inner and outer cylinders 330, 332 at the distal opening 344 towards the desired viewing field.

In one embodiment, the system 300 further comprises one or more illumination ports 348 in the sheath intermediate portion 304 that are optically coupled to proximal ends of one or more of the optical fibers 336.

In a second embodiment, the system 300 further comprises an illumination source or guide 350 optically coupled to the one or more illumination ports 348. In one implementation, the one or more illumination ports 348 are openings in the outer cylinder 332 of the sheath.

In one embodiment, the system 300 further comprises one or more fluid ingress ports 352 in the sheath intermediate portion 304. In one implementation, the one or more fluid ingress ports 352 are located distally in relation to the one or more illumination ports 348.

In one example, a fluid ingress port 352 is an opening in the inner and outer cylinders 330, 332 of the sheath 326. In one embodiment, the system 300 also comprises an interface 354 to one or more fluid communication components 356. In one implementation, the interface 354 is a rotatable and detachable stopcock collar. In one example, the interface 354 operatively couples the one or more fluid communication components 356 to the one or more fluid ingress ports 352.

In one embodiment, the system 300 further comprises one or more fluid egress ports 358 in the sheath intermediate portion 304 or distal end 324.

In one configuration, the spacing 360 between the inner cylinder 330 of the sheath and an exterior surface 362 of the endoscope 302 forms one or more irrigation channels between the one or more fluid ingress ports 352 and the one or more fluid egress ports 358.

In one example, the one or more fluid egress ports 358 are located at one or more points or planes of tangency 334 between the inner and outer cylinders 330, 332. In a second example, the one or more fluid egress ports 358 are located near the sheath distal end 324.

In one embodiment, the body 306 comprises a proximal eyepiece 361 for viewing images. In one implementation, the optical path 322 extends through the endoscope 302 to the proximal eyepiece 362. In one example, the body 306 further comprises a proximal ocular lens 363 situated along the optical path 322.

In one embodiment, the body 306 comprises first and second connectable and detachable portions 364, 366, with the first portion 364 affixed to or integral with the proximal end 312 of the endoscope, and the second portion 366 affixed to or integral with the proximal end 328 of the sheath. In one implementation, the first portion 364 is recessed to receive the second portion 366. In one example, the first portion 364 includes a latch mechanism 388 for detachably latching the second portion 366 to the first portion 364.

In one embodiment, the first body portion 364 affixed to or integral with the endoscope 302 comprises the endoscope 100 illustrated in FIGS. 1–3, and the second body portion 366 affixed to or integral with the endoscope sheath 326 comprises the endoscope sheath 200 illustrated in FIGS. 4–8.

In one embodiment, the placement of optical fibers in the sheath rather than the endoscope eliminates the need for low temperature soldering of the distal window to the distal end of the endoscope, thus avoiding the attendant oxidation of and buildup of solder material on the distal window, and allows the use of high temperature brazing to adhere the distal window to the endoscope.

In another embodiment, the use of a large-diameter objective lens assembly allows high resolution viewing of body structures through the proximal eyepiece of the endoscope.

In a third embodiment, the use of an image relay assembly having a smaller diameter than that of the objective lens assembly avoids the restriction in irrigation fluid flow that could otherwise occur if the diameters of the two assemblies were the same.

In a fourth embodiment, the placement of a fluid egress port at a point or plane of tangency between the eccentrically-arranged inner and outer cylinders of the sheath, coupled with the placement of the optical fibers in an annular gap between the cylinders, avoids the need to route the fibers to avoid this fluid egress port.

In a fifth embodiment, the distal placement of a fluid egress port in relation to an illumination port in the endoscope sheath allows an illumination source or guide coupled to the illumination port to be placed close to the camera and thus used by the surgeon during the surgical procedure as a handle or guide for holding or placing the endoscope-sheath system.

Other advantages and benefits may be possible, and it is not necessary to achieve all or any of these benefits or advantages in order to practice the invention as claimed. Therefore, nothing in the foregoing description of possible or exemplary advantages and benefits can or should be taken as limiting.

EXAMPLE

In an example of an endoscope-sheath system according to the invention, the endoscope and sheath couple together and collaborate in use. The endoscope consists of image rely optics with an objective lens at the distal end, an image relay intermediate, and an ocular at the proximal eyecup. When coupled to a camera head, the image sensed by an image pickup device such as a CCD.

The scope, consisting of image optics only (no illumination fibers), houses the optic elements in an elongated hollow shaft of minimum diameter, which is dictated by the size of the optics and the tube thinness. However, the objective lens may be oversized with respect to the majority of the tip length as to provide greater optical performance. Since the majority of tip length is of minimum diameter, fluid irrigation, in the annular space between the scope and sheath, is accommodated with minimum sheath size.

The scope has a distal end of larger diameter wherein the objective lens(es) are captive behind the distal window of a sapphire negative. Without fiber optics for illumination, the sapphire negative is bonded with a high temperature braze which is a chemically stable and durable material resisting the harsh chemical environments and sterilization processes typically experienced by such instruments. The optics of the oversized distal end segment is housed in an adapter that fits over the elongated optical tubing of the scope and is welded at the external proximal seam of the adapter. The window is of a relatively large size and is directly seated and joined to the objective housing with no intermediate parts. The distal window, being oversized and flat at the end, supports increased image quality in that the window is easier to clean and less likely to attract debris, and because the objective lens can be larger.

The scope interfaces to the sheath by a plug and socket automatic locking mechanism. An elastomeric seal is used for compression while a latch mechanism of the socket component engages to a slot on the diameter of the plug member of the mating component. The mechanism automatically engages during insertion with an appropriate axial load. The light post extending in a generally radial direction from the interfacing diameter of the plug member, is self-guiding into a radial cutout profile of the socket member. During insertion, the radial protrusion (stopcock body or light post) is guided into the cutout of the socket in an instinctive way that results in radial alignment of the scope with respect to the sheath when engagement is reached. The scope is released from the sheath by depressing the latch of the socket member. The axial interface of the plug and socket members is sufficient to the extent that any bending loading on the sheath tip will be transferred to the body of the scope rather then the more vulnerable tip housing the optical components.

The sheath provides scope protection, facilitates fluid irrigation, and provides light illumination wherein fiber optics are routed from a location on the sheath body to terminate at the distal opening of the sheath. The fibers of the sheath are contained between two eccentric tubes and are polished flush within the gap at the opening of the distal end.

Fluid flow is provided through the inner space of the sheath and exits through the distal opening. The sheath size is determined by the amount of illumination fibers needed, appropriate flow area, and sufficient thickness for the tubes which house the fiber and protect the scope when a bending load is applied to the system.

Around the distal opening of the sheath the fibers extend to the gaps between the inner and outside tube of the sheath tip. As the tips are of a formed radius, especially on the bottom side, the fibers are directed toward the field of view. Thus the design naturally accommodates correct field illumination for imaging. At the opening wherein the fibers are displaced, the fibers are cemented with epoxy and polished flush as to leave no small openings that could be a place for bacteria to reside.

An additional aspect of the distal end configuration of the scope and sheath is that the scope remains recessed (or shrouded) behind the distal opening of the sheath while at the same time the inside walls of the sheath do not obstruct the view of the scope. The adequate yet not excessive recession of the scope allows for protection of the scope window from collision with aggressive operative instrumentation such as shaver blades and burrs. To hold the scope end in position within the larger internal diameter of the sheath, the internal tube of the sheath is indented as to fix the scope in tangency in alignment with the opening. Thus, the scope end has limited movement so as to be protected by the sheath while retaining full view of the objective lens at the distal window.

While the distal end configuration of the scope and sheath provide for an outflow gap between the distal end of the scope and the distal opening of the sheath, an opening is provided through the walls of the sheath at the point of tangency of the sheath tubes and at a location near the distal end proximal to the oversized diameter. The axial elongated hole or fenestration compensates for the increased scope diameter of the distal end by adding the outlet opening prior to the reduction in flow area caused by the oversized scope end.

This example integrates both the fiber optic illumination and the fluid coupling in the sheath that attaches to a reduced diameter scope (with image optics only). The interfacing means comprises a latch mechanism on the distal portion of the scope body rather than on the sheath. A plug and socket mechanism is employed, with the sheath plugging into the socket in the scope body. The light guide of the sheath is self-orientating by a radial slot in the socket of the scope body.

This example has fluid coupling more distal with respect to the light post and permits the stopcock to rotate as is normally desired. Although displaced on the sheath, the light post can function as a lever arm. In addition the stopcock is removable and has 360-degree rotation.

To facilitate fluid communication through a stopcock distal to the light input, the inner and outer tubing encasing the light fibers are penetrated at the location where the stopcock couples onto the sheath body. The opening into the tube structure is centered at the location where the two tubes of the sheath are tangent to not sever the light fibers contained within the tubing. This opening is elongated only in the axial direction of tube tangency to provide the necessary inflow area for minimum impedance.

While various embodiments of the invention have been described, it will be apparent to those of ordinary skill in the art that many more embodiments and implementations are possible that are within the scope of this invention.

What is claimed is:

1. An endoscope comprising:
   an intermediate portion having a distal end;
   one or more optical elements forming an objective lens assembly having a first diameter, the objective lens assembly disposed at or within the distal end; and
   one or more optical elements forming an image relay assembly having a second diameter less than the first diameter, the image relay assembly disposed at or within the intermediate portion and situated along an optical path extending from the objective lens assembly,
   wherein the distal end at least partially houses the objective lens assembly, and the intermediate portion at least partially houses the image relay assembly,
   wherein the distal end is a tube or tube segment, and the intermediate portion is a tube or tube segment,
   wherein the distal end tube or tube segment has an inner diameter defining the first diameter of the objective lens assembly, and the intermediate portion tube or tube segment has an inner diameter defining the second diameter of the image relay assembly, and
   wherein the intermediate portion tube or tube segment has an outer diameter approximately equal to the inner diameter of the distal end tube or tube segment, and the distal tube or tube segment closely receives in axial alignment an interface portion of the intermediate tube or tube segment.

2. The endoscope of claim 1 wherein the distal end tube or tube segment has an inner surface adhered to an outer surface of the interface portion of the intermediate portion tube or tube segment.

3. The endoscope of claim 2 wherein the distal end tube or tube segment is a metal tube or tube segment, and the inner surface thereof is welded to the outer surface of the interface portion of the intermediate portion tube or tube segment, also a metal tube or tube segment.

4. An endoscope-sheath system comprising:
   an endoscope having an axis and comprising: (1) an intermediate portion having a distal end and a proximal end; (2) one or more optical elements forming an objective lens assembly having a first diameter in a plane perpendicular to the axis, the objective lens assembly disposed at or within the distal end; and (3) one or more optical elements forming an image relay assembly having a second diameter less than the first diameter, the image relay assembly disposed at or within the intermediate portion and situated along an optical path extending from the objective lens assembly, the image relay assembly being in alignment with the axis;
   an endoscope sheath sheathing at least a portion of the endoscope comprising: (1) a distal end, an intermediate portion, and a proximal end, with inner and outer cylinders eccentrically arranged to contact one another at one or more planes of tangency, thus forming one or more annular gaps in between the inner and outer cylinders; and (2) a plurality of optical fibers extending lengthwise through the one or more annular gaps from the distal end through at least a part of the intermediate portion; and
   a body affixed to or integral with the proximal ends of the endoscope and endoscope sheath.

5. The system of claim 4 wherein the endoscope distal end is a tube or tube segment at least partially housing the objective lens assembly, and the endoscope intermediate portion is a tube or tube segment at least partially housing the image relay assembly.

6. The system of claim 4 wherein the endoscope distal end has a distal window through which light reflected from an object in the field of the view of the endoscope enters the endoscope.

7. The system of claim 6 wherein the distal window is adhered to the endoscope distal end tube or tube housing.

8. The system of claim 7 wherein the endoscope distal end comprises a metal tube or tube segment and the distal window is brazed to the endoscope distal end tube or tube segment.

9. The system of claim 8 wherein the distal window is composed of glass or sapphire.

10. The system of claim 6 wherein the endoscope distal window is situated within or optically coupled to the sheath distal window.

11. The system of claim 10 wherein the sheath distal end has an end form that angles the distal opening towards a desired viewing field.

12. The system of claim 11 wherein the end form also angles the one or more angular gaps between the inner and outer cylinders at the distal opening towards the desired viewing field.

13. The system of claim 4 further comprising an illumination port in the sheath intermediate portion optically coupled to proximal ends of one or more of the optical fibers.

14. The system of claim 13 further comprising one or more illumination sources or guides coupled to the one or more illumination ports.

15. The system of claim 13 further comprising one or more fluid ingress ports in the sheath intermediate portion.

16. The system of claim 15 wherein the one or more fluid ingress ports are located distally in relation to the one or more illumination ports.

17. The system of claim 15 wherein the one or more fluid ingress ports are openings in the inner and outer cylinders of the sheath.

18. The system of claim 17 further comprising an interface to one or more fluid communication components.

19. The system of claim 18 wherein the interface is a rotatable and detachable stopcock collar.

20. The system of claim 18 further comprising one or more fluid communication components operatively coupled to one or more fluid ingress ports.

21. The system of claim 13 further comprising one or more fluid egress ports in the sheath intermediate portion.

22. The system of claim 21 wherein spacing between the inner cylinder of the sheath and an interior surface of the endoscope forms one or more irrigation channels from the one or more fluid ingress ports to the one or more fluid egress ports.

23. The system of claim 21 wherein the one or more fluid egress ports are located at one or more points or planes of tangency between the inner and outer cylinders.

24. The system of claim 23 wherein the one or more fluid egress ports are located near the sheath distal end.

25. The system of claim 4 wherein the one or more illumination ports are openings in the outer cylinder of the sheath.

26. The system of claim 25 wherein the one or more illumination ports further comprise openings extending from a recessed portion of the body to an exterior surface of the body.

27. The system of claim 4 wherein the body comprises a proximal eyepiece for viewing images.

28. The system of claim 27 wherein the optical path extends through the endoscope to the proximal eyepiece.

29. The system of claim 28 wherein the body further comprises a proximal ocular lens situated along the optical path.

30. The system of claim 4 wherein the body comprises first and second connectable and detachable portions, the first portion affixed to or integral with the proximal end of the endoscope, and the second portion affixed to or integral with the proximal end of the sheath.

31. The system of claim 30 wherein the first portion is recessed to receive the second portion.

32. The system of claim 31 wherein the first portion includes a latch mechanism for detachably latching the second portion to the first portion.

33. An endoscope-sheath system comprising:
an oblique viewing endoscope component having a proximal housing, proximal opening into an interior of said proximal housing, a hollow shaft extending distally from the proximal housing, said hollow shaft having open ends including a distal opening, said hollow shaft having a distal portion housing objective lens elements, said hollow shaft having an intermediate portion housing additional image transmission elements, whereas an outside diameter of said distal portion is larger than an outside diameter of said intermediate portion and whereas the objective lens elements housed in said distal portion are larger in diameter than said image transmission elements housed in said intermediate portion, and having means by which an image of an object adjacent to the distal opening of said hollow shaft can be viewed through said proximal opening;
a sheath component having a hollow interior, a proximal body with an opening on the proximal end, an illumination input on said body, a tip extending distally from said body, said tip comprising a hollow interior with an opening on the distal end, said tip further comprising a housing which contains illumination elements, said illumination elements transmitting light from said illumination input to the distal opening of said tip, an irrigation channel through the hollow interior of said sheath having fluid communication from said distal opening of said tip to a proximal interior of said body, fluid communication means from the proximal interior of said body to external fluid port(s), said hollow shaft of said endoscope component being removably inserted through the proximal opening of said sheath component, and means by which said sheath component interfaces with and is removably attached to said endoscope component, and having a distal end that, when attached with said endoscope component, corresponds, within several mm, to the distal end of said endoscope component; and
a fluid communication component having a port accessible on an exterior of said sheath component of said endoscope component and having fluid communication with said hollow interior of said sheath component.

34. An endoscope-sheath system as defined in claim 33, regarding the endoscope component, the objective optical elements comprising a distal element, with a outside window a negative surface internally, a subsequent prism, and a field lens proximal whereas the elements are cemented together as a single unit (compound lens).

35. An endoscope-sheath system as defined in claim 33, regarding the endoscope component, said intermediate and said distal portions of said hollow shaft are straight metal tubes.

36. An endoscope-sheath system as defined in claim 35, the internal diameter of the tube defining the intermediate portion of said hollow shaft correspond to the diameter of said image transmission optics housed within and the internal diameter of the tube defining said distal portion of said hollow shaft being nearly essentially equivalent to the diameter of said objective lens elements.

37. An endoscope-sheath system as defined in claim 36, whereas the internal diameter of the tube defining said distal portion of said hollow shaft is equivalent to the outside diameter of the tube defining said intermediate portion.

38. An endoscope-sheath system as defined in claim 37, the interface of said straight metal tubes is defined by the inside diameter of the larger distal tube closely receiving the outside diameter of the smaller tube comprising the intermediate portion of said hollow shaft.

39. An endoscope-sheath system as defined in claim 38, the said straight metal tubes being joined together by a weld located on the outside seam defined by said interface.

40. An endoscope-sheath system as defined in claim 37, further regarding the sheath component, whereas the fluid communication component is displaced on said body of the sheath component and located distally with respect to said illumination input.

41. An endoscope-sheath system as defined in claim 40, whereas the more proximal illumination input is an external light post connector adapted to receive a light guide.

42. An endoscope-sheath system as defined in claim 41, the endoscope component further comprising a socket member with latching mechanism for attachment to said sheath component wherein said proximal end of said body is adapted as a plug interfacing with said socket member and said light post connector locks into a radial opening blended into the distal opening of said socket member for holding the orientation of the endoscope component fixed with respect to the sheath component.

43. An endoscope-sheath system as defined in claim 42, whereas the fluid communication component comprises a component that is removably attached to said sheath component in a coaxial manner and allowing the fluid communication component full rotation around the axis of attachment.

44. An endoscope-sheath system as defined in claim 43, whereas the fluid communication component comprises a component that is removably attached to said sheath component in a coaxial manner and allowing the fluid communication component full rotation about the axis of attachment.

45. An endoscope-sheath system as defined by claim 33, further comprising means to prevent said sheath component from rotating with respect to said endoscope component when attached.

46. An endoscope-sheath system as defined by claim 33, said endoscope component having a transparent distal window joined within the distal opening of said hollow shaft and hermetically sealing said interior from the outside environment.

47. An endoscope-sheath system as defined in claim 46, said distal window having a convex surface on the proximal side/internal surface.

48. An endoscope-sheath system as defined in claim 47, said distal window is of glass or sapphire.

49. An endoscope-sheath system as defined in claim 48, said distal window is joined to said distal portion of said hollow shaft by brazing.

50. An endoscope-sheath system as defined by claim 33, regarding the endoscope component, wherein said image transmission optics proximal to said objective lens elements is composed of lens relay system of rod lenses.

51. An endoscope-sheath system as defined by claim 33, regarding the endoscope component, wherein said image transmission optics proximal to said objective lens elements is composed of an optical fiber bundle.

52. An endoscope-sheath system as defined by claim 33, said endoscope component further comprising a cylindrical reinforcement member over a most proximal portion of said hollow shaft, extending from said proximal housing and terminating subsequent to the position of flow communication corresponding to position of said fluid port when attached to said sheath component.

53. An endoscope-sheath system as defined by claim 33, said endoscope component further comprising an eyepiece on said proximal end of said housing.

54. An endoscope-sheath system as defined by claim 33, said endoscope component further comprising an ocular lens within said interior near said proximal end for viewing the image through said proximal end.

55. An endoscope-sheath system as defined by claim 33, said fluid communication component further comprising an external valve adjacent to said port whereas said external valve can be manually actuated to initiate or cease fluid communication.

* * * * *